United States Patent [19]

Prause

[11] 4,254,660
[45] Mar. 10, 1981

[54] ULTRASONIC TEST METHOD AND APPARATUS WITH COUPLING LIQUID TEMPERATURE COMPENSATION

[75] Inventor: Reinhard Prause, St. Augustin, Fed. Rep. of Germany

[73] Assignee: Krautkramer-Branson, Inc., Stratford, Conn.

[21] Appl. No.: 95,344

[22] Filed: Nov. 19, 1979

[30] Foreign Application Priority Data

Jan. 19, 1979 [DE] Fed. Rep. of Germany ....... 2902017

[51] Int. Cl.³ ............................................. G01N 29/00
[52] U.S. Cl. ........................................ 73/597; 73/622
[58] Field of Search ................. 73/597, 602, 609, 610, 73/618, 622, 625, 1 DV, 290 V

[56] References Cited

U.S. PATENT DOCUMENTS

| 3,828,609 | 8/1974 | Furon et al. | 73/622 |
| 3,848,460 | 11/1974 | Bantz et al. | 73/597 |
| 3,850,026 | 11/1974 | Lund et al. | 73/622 |

OTHER PUBLICATIONS

H. E. Gundtoft et al., *Materialpruefung*, vol. 19, No. 9, pp. 385–388, Sep. 1977.

*Primary Examiner*—Stephen A. Kreitman
*Attorney, Agent, or Firm*—Ervin B. Steinberg; Philip J. Feig

[57] ABSTRACT

In an ultrasonic pulse-echo test measuring or gaging system wherein a workpiece is coupled to the ultrasonic transducer by a liquid coupling medium, the temperature of the liquid affects precise measurement of the workpiece as the acoustic velocity of a liquid changes with temperature. To compensate for the change of acoustic velocity during measurement periodically a search pulse is transmitted along its normal path over a calibrated fixed distance. The resulting transit time value is converted to a distance value and compared witht the calibrated distance value. Any difference in the values updates a compensation factor which subsequently is used in the test system. Periodic updating may be set to occur, for example, every one-half second.

8 Claims, 1 Drawing Figure

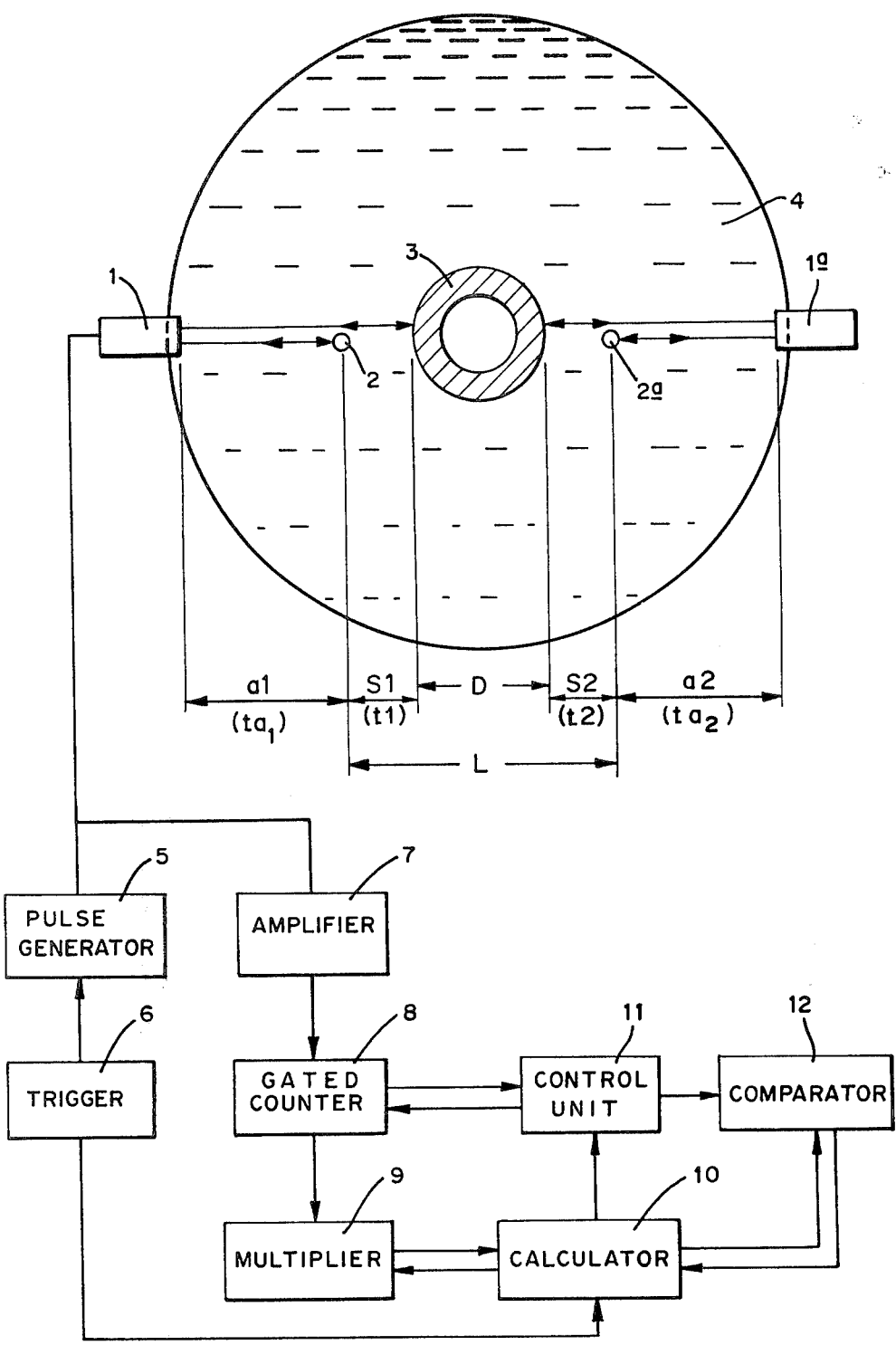

ULTRASONIC TEST METHOD AND APPARATUS WITH COUPLING LIQUID TEMPERATURE COMPENSATION

BACKGROUND OF THE INVENTION

This invention concerns a method and apparatus for testing workpieces with ultrasonic energy and more specifically concerns a method and apparatus for compensating for changes of the sound velocity of the coupling liquid as a function of temperature.

When testing workpieces with ultrasonic energy the energy is cyclically transmitted from an electroacoustic transducer to the workpiece via a coupling liquid, mostly water. The ultrasonic energy transmitted is reflected at the workpiece surface, at an acoustic discontinuity within the workpiece and also at the rear surface of the workpiece. The reflected energy is transmitted back to the transmitting transducer or to a separate receiving transducer and is converted by the transducer to an electrical signal which, in turn, is sent to an evaluation circuit. The transit time of the ultrasonic pulse while transversing the coupling liquid is an important parameter for determining the geometry of the workpiece under test.

In ultrasonic test systems the workpiece is frequently moved at a substantially high speed relative to the transducer. Relative motion may comprise one or more transducers being rotated about a workpiece, a linear motion of transducers parallel to the workpiece surface, or a combined rotational and linear motion, i.e. helical scan. In a typical arrangement for testing tubes or cylindrical workpieces ultrasonic transducers are rotated about the workpiece while the workpiece is translated in the axial direction. Such test arrangements are used to determine the inner and outer diameters and the eccentricity, particularly the degree of out-of-roundness, by measuring the transit time of the ultrasonic signal traversing the coupling medium and the wall of such a tubular workpiece.

When it is desired to use such rotational arrangements for determining with a high degree of precision the out-of-roundness and the outer diameter of a tubing or cylinder an important requirement is that the acoustic velocity of the coupling liquid remain constant during the measuring period. However, given the changes arising from the working environment such constant conditions are not possible. Therefore, it is required that the influence of the temperature, i.e. the temperature responsive change of the sound velocity of the coupling liquid, be compensated. For instance, using water, the velocity of sound changes at the rate of 2.5 meter per second per degree K. Assuming a nominal sound velocity of 1480 meter per second, room temperature, and a liquid coupling path of 15 mm, a measuring error of 0.051 mm per degree K. occurs for each coupling path, however is must be kept in mind that the total ultrasonic signal path distance is 30 mm, i.e. 15 mm gap distance which must be traversed by the acoustic pulse in both directions. If two diametrically opposite measuring paths are used as is commonly the case, the measuring error amounts to approximately 0.1 mm per degree K. Systems currently in use permit, however, a measuring accuracy of a few thousandth mm.

For overcoming the temperature induced variation of the sound velocity in the coupling path, two solutions are known.

In the first arrangement regulating means are used to maintain the temperature of the coupling liquid constant to the extent of a few tenth degree K. This method is slow and it is necessary to adapt the system to the prevailing test conditions. A temperature sensor must be provided in the liquid which controls the heating or cooling of the liquid. The temperature of the coupling liquid is controlled from sources independent of the measuring arrangement.

In the second arrangement the changes of sound velocity are compensated. For this purpose an auxiliary measuring distance comprising a transducer and reflector, independent of the actual measuring path, is provided within the coupling liquid and the transit time of ultrasonic energy traversing this path is measured on a continuous basis. In order to avoid determining the precise sound velocity only the temperature responsive transit time change is considered and, hence, a distance compensation distance is required which is adjusted by means of very complicated and highly precise mechanical means to provide an auxiliary measuring distance exactly equal to the sum of both coupling paths between the respective transducers and the workpiece surface. The disadvantage of this arrangement resides in the fact that there usually is little space for such auxiliary measuring means between the rotating workpiece and the transducer disposed in close proximity thereto.

Moreover, the auxiliary arrangement requires a separate electronic circuit, see H. E. Gundtoft et al, Materialpruefung 19 (1977) No. 9, pp. 385-388.

Compensation by the use of separate temperature sensors is also disadvantageous since further means are needed within the coupling liquid in close proximity to the measuring path and compansation requires the use of a function table (i.e. electronic memory) which provides the sound velocity as a function of the temperature measured.

Another known system used primarily in rotating test systems utilizes auxiliary reflectors disposed in the sonic energy path between the measuring transducers and the rotating workpiece, and for shortening the actual measuring path such reflectors are located very close to the workpiece surface. The distance of these reflectors to the transducer is either predetermined or is adjustably fixed.

The functional significance of the auxiliary reflector is not considered further herein inasmuch as this is not important for this invention. If the auxiliary reflectors are not present in a system, they can be installed in the sonic energy path without any problem since no electrical connections are necessary. With regard to such auxiliary reflectors reference is made to Gundtoft supra and German OS No. 21 48 976.

SUMMARY OF THE INVENTION

The present invention concerns an arrangement in which temperature compensation of the sound velocity of the coupling liquid is achieved in a simpler and more economical manner. The system described hereafter provides that the temperature responsive measurement error, when converted to units of workpiece length, does not exceed the magnitude of a few thousandth mm.

In accordance with the present invention at least one auxiliary reflector is located in the coupling liquid at a predetermined location within or close to the acoustic energy path from the test transducer to the workpiece to thereby provide a calibrated distance. During measurement of the workpiece, periodically the transit time of the ultrasonic signal across this calibrated distance is determined and multiplied by the value for the velocity of sound in the liquid established during calibration to derive an apparent distance value. By forming the quotient between said apparent distance value and the calibrated distance value established during calibration a correction factor is derived which is stored. This factor is used during the ensuing transit time measurements of the acoustic signal across the liquid coupling path from the transducer to the workpiece surface as a multiplier for providing the temperature corrected distance from the transducer to the workpiece surface.

BRIEF DESCRIPTION OF THE DRAWING

The single FIGURE is a schematic illustration of a preferred embodiment of the present invention.

DETAILED DESCRIPTION OF THE INVENTION

Workpieces in the form of a cylindrical tubing 3 disposed in a liquid 4 are tested by one or more ultrasonic transducers 1, 1a which are mounted for rotation about the workpiece. For explaining the present temperature compensation arrangement only one acoustic energy path, coupling distance S1, is considered.

Test transducer 1 receives from a pulse generator 5 an electrical pulse signal and in response to such electrical signal transmits an acoustic pulse signal toward the workpiece 3. This acoustic signal is reflected first at the auxiliary reflector 2 which is disposed in the acoustic measuring path and then at the surface of the workpiece 3. The reflected or echo signals reaching the transducer 1 are converted by the transducer to electrical signals and processed in the electronic circuit comprising blocks 7 through 12. Separate transducers could be used for receiving the echo signals. The workpiece testing arrangement is considered hereinafter only to the extent necessary for dealing with the temperature dependent compensation of the sound velocity of the liquid coupling medium 4.

For calibration of the test arrangement a calibration tubing or calibration bar of precisely known diameter, usually to 1 μm measured accuracy, is used. This calibration tubing or bar is used in the arrangement shown to measure the distances S1 and S2 within the coupling medium 4 for determining the transit times t1 and t2 of the ultrasonic signal. The distance L between both auxiliary reflectors 2, 2a is given by:

$$L = D + v_k[t1(T_k) + t2(T_k)] \qquad (1)$$

wherein $v_k$ equals the velocity of sound in the liquid medium 4 at calibration temperature, $t(T_k)$ is the transit time of the acoustic energy at calibration temperature, and since $D = L - (S1 + S2)$ as shown in the figure, and $S1 + S2$ can be replaced by:

$$v_k[t1(T_k) + t2(T_k)].$$

For determining during calibration the velocity of sound $v_k$ in the coupling liquid 4 several possibilities exist:

1. The distance a1 or a2 is determined by a one time precise mechanical measurement using the transit time $ta_{1,2}(T_k)$ to derive $v_k = a1,2/ta_{1,2}(T_k)$. It is advantageous if the auxiliary reflector 2 or 2a is fixedly connected to the respective transducer 1 or 1a.

2. In the event that the positioning of the elements 1, 2, 1a and 2a is not movable and the distances are known from precise mechanical measurement, the acoustic velocity can be measured for calibration purposes by use of the calibration workpiece following the equation (1), that is:

$$v_k = \frac{L - D}{t1(T_k) + t2(T_k)}$$

3. It is possible further to determine the acoustic velocity by a precise temperature measurement of the coupling liquid 4.

The change of sound velocity as a function of temperature for the particular coupling medium is available as a mathematical relation from published tables.

4. The acoustic velocity of the coupling liquid can be determined also from the ratio of two distances. If for instance $a1 \neq a2$ then $a1 - a2 = \Delta a$. This value can be determined also from mechanical measurement. Resulting from the transit time differences $$ta_1(T_k) - ta_2(T_k) = \Delta t_k$$

$$v_k = \Delta a / \Delta t_k$$

5. If two tandem placed auxiliary reflectors are disposed in the test path, the acoustic velocity can be determined from the distance between the two reflectors, which distance must be measured mechanically with precision, and from the temperature responsive transit time of the echo signals between the two reflectors.

For compensating the temperature dependent change of the sound velocity in the coupling liquid in accordance with the present invention on a continuing basis only a portion of the test arrangement shown is used, such as transducer 1 in combination with the auxiliary reflector 2. The distance between the transducer 1 and the reflector 2 is either predetermined, i.e. nonadjustably fixed or adjustably fixed. Since during calibration and at the then prevailing temperature of the coupling liquid 4 the velocity of sound in the liquid was determined, the following transit time relation between the transducer 1 and the auxiliary reflector 2 is apparent:

$$ta_1(T_k) = a1/v_k$$

Assuming a transit time t(T) at temperature T and an acoustic velocity v(T) in the coupling distance at temperature T, and assuming, moreover, that the transit times reflect only the path of a signal through the respective distance in one direction, then for another operating temperature which differs from the temperature at which calibration of the workpiece diameter occurred the following applies:

$$D = L - v(T) \cdot [t1(T) + t2(T)] \qquad (2)$$

whereas for the temperature at which calibration occurred the following condition applied:

$$D = L - v_k[t1(T_k) + t2(T_k)].$$

Using a compensation factor $$m = v(T)/v_k$$

it follows from equation 2

$$D = L - m \cdot v_k[t1(T) + t2(T)] \quad (3)$$

and since $$a1 = v_k \cdot ta_1(T_k) = v(T) \cdot ta_1(T)$$

it follows:

$$m = v(T)/v_k = ta_1(T_k)/ta_1(T) \quad (4)$$

The quotient on the right side of equation 4 comprises time intervals which are capable of being measured for the distance a1. If equation (3) is multiplied by the compensation factor in the parentheses, then $$D = L - v_k[m \cdot t1(T) + m \cdot t2(T)]$$

The compensation factor m can be determined during compensation shots which are interposed in a suitable time frame between the measuring shots.

It is possible also to provide calibration during the measuring shot when using suitable timing gates. The term calibration shot or measuring shot shall designate the transmission of an ultrasonic search signal and receipt of the subsequent echo signal.

The FIGURE shows a digital electronic circuit as a typical embodiment. A trigger 6 controls a pulse generator 5 which applies an electrical pulse signal to the transducer 1. The transducer in response to the electrical pulse transmits an ultrasonic search signal which is reflected at the auxiliary reflector 2 and received, in turn, as an echo signal at the transducer 1. This cycle of events can be repeated from a few hundred to several thousand times per second. Trigger 6 provides also a synchronizing signal to the calculator 10. The echo signal received by transducer 1 is transformed to an electrical signal which is amplified in amplifier 7 and fed to a gated counter 8. The counter counts at a high pulse rate, e.g. 500 MHz, the transit time of the pulse signals, in the present instance, the time interval between the transmission of the search signal and the receipt of the reflected signal from reflector 2. The count generated in the counter 8 and representing transit time is provided to the multiplier 9. The count value representing transit time is multiplied in the multiplier 9 by the stored value $v_k$ representing the acoustic velocity of the liquid coupling means and derived during calibration.

Hence, the product derived from the multiplier represents the apparent distance traversed by the acoustic signal. This distance value is supplied to the calculator 10 and multiplied by the compensation factor m stored in the calculator. The distance value derived in the calculator 10 is fed to the comparator 12 in which the calibrated distance value a1 is stored and compared with the value representing the measured distance a1. If a difference is present between the measured distance and the calibrated distance, the comparator 12 provides correction signals to the calculator 10 until the difference is zero whereupon calculator 10 is provided with an updated temperature correction factor m usable for the ensuing measurements of the acoustic velocity or transit times respectively needed to determine the dimensions of the workpiece. In a typical embodiment, the compensation factor updating measurement is made every one half second, that is, after the passage of 5,000 measuring shots a compensation shot is transmitted. The change from measurement shots to a compensation shot is accomplished by a control signal from the control unit 11 to the gated counter 8 which gates the respective time intervals, i.e. the distance from the transducer 1 to the reflector 2 or from the transducer to the workpiece surface. The conductor from counter 8 to the control unit 11 provides an answering signal confirming that the instruction to the gated counter 8 has been carried out. The control unit 11 is triggered periodically by the calculator 10. In the interval between compensation shots a stored factor m is used for the calculation but as shown this factor is updated every one-half second or more often if so desired.

The conductor from the calculator 10 to the multiplier 9 serves to insert the coupling medium velocity value $v_k$ determined during calibration into the multiplier before the start of the measurement process.

In an alternative embodiment, the calculator 10 and the multiplier 9 can comprise a single unit.

In other embodiments which do not use digital circuits for the distance a1 or for the time $ta_1$, and for the distance S1 or t1 respectively, separate gates may be used to derive a compensation factor responsive to distance a1 or time $ta_1$.

Any of the above stated methods will suffice for determining the acoustic velocity $v_k$ of the coupling medium during the required calibration procedure.

The heretofore described method and apparatus for compensating the influence of temperature of the coupling liquid upon the acoustic velocity obviates the need for disposing complex elements in the acoustic path, thus compensation is achieved in a simpler manner than the methods used heretofore. Only an electronic control unit 11 is required in order to incorporate the above stated compensation procedure in the digital circuit normally provided for measuring workpieces by the ultrasonic pulse echo method.

What is claimed is:

1. The method for compensating for the temperature responsive changes of the acoustic velocity in a liquid used in an ultrasonic test system wherein cyclically an ultrasonic search signal is transmitted from an ultrasonic transducer through a liquid coupling medium to a workpiece and the echo signals arising from reflections of the search signal at the workpiece surfaces are used for evaluating the workpiece dimensions and wherein along the search signal path from said transducer to the workpiece an auxiliary reflector is disposed at a fixed distance from said transducer, the steps comprising:

periodically transmitting a further search signal from said transducer along said signal path and receiving echo signals arising from said further signal being reflected along said path;

providing a first output value responsive to the transit time of said further search signal traversing said fixed distance from said transducer to said reflector;

multiplying said first output value by an acoustic velocity value of the liquid medium obtained during a calibration procedure to thereby obtain a second output value;

multiplying said second output value by a stored compensation factor to obtain a third output value;

comparing said third output value with a stored distance value representing said fixed distance and obtained during a calibration procedure and updating said stored compensation factor responsive to any difference between said third output value and said stored distance value, and storing said updated compensation factor and utilizing it in succeeding search signal transmissions used for evaluating the workpiece dimensions until a subsequent further search signal causes once again updating of said compensation factor.

2. The method as set forth in claim 1 and for calibrating purposes inserting a calibrated cylindrical workpiece in said signal path and determining the length of said fixed distance and the velocity value of the coupling medium from the respective acoustic transit times of a search signal from said transducer to said reflector and to the surface of said calibrated workpiece.

3. The method as set forth in claim 1 and determining during calibration the value of the acoustic velocity of the coupling medium by measuring the temperature of said medium and deriving the acoustic velocity value pertaining to the measured temperature from the known relationship.

4. The method as set forth in claim 1 and determining during calibration the acoustic velocity value of the coupling medium from the constant difference between two measured distances and the temperature responsive transit time difference of the acoustic signal between said measured distances.

5. The method as set forth in claim 1 and determining the acoustic velocity value of the coupling medium during calibration from the distance between two tandem disposed reflectors in the search signal path and the temperature responsive transit time of the acoustic signal between these reflectors.

6. In an ultrasonic pulse-echo system wherein a workpiece is acoustically coupled by a liquid coupling means to an ultrasonic transducer means which cyclically transmits an ultrasonic search pulse signal through the liquid coupling means to the workpiece and echo signals arising from the search signal being reflected by the workpiece are processed for evaluating the dimensions of the workpiece, the combination of:

at least one auxiliary reflector disposed along the search signal path from said transducer means to the workpiece at a fixed distance from said transducer means;

pulse means coupled to said transducer means for cyclically causing said transducer means to transmit an ultrasonic search signal along said search signal path toward the workpiece;

control means;

timing means coupled to said transducer means and said control means for providing responsive to the operation of said control means either a first output signal responsive to the transit time of the search signal from said transducer means along said fixed distance to said reflector or a second output signal responsive to the transit time of the search signal from said transducer means to the workpiece; calculating means coupled for receiving said first output signal and multiplying it by a stored value representing the acoustic velocity of said medium at calibrated condition and multiplying the product derived by a stored compensation factor to thereby obtain a value indicative of said fixed distance;

comparing means coupled for receiving said value indicative of said fixed distance and for comparing it with a stored value denoting the calibrated distance and providing a feedback signal responsive to the difference between said values;

means for applying said feedback signal to said calculating means to cause an updated compensation factor by correcting said value indicative of said fixed distance until it equals the stored value denoting the calibrated distance, and said control means responsive to updating said correction factor causing said timing means to provide said second output signal to said calculating means for processing said second output signal with said updated correction factor to obtain information responsive to the workpiece dimension.

7. In an ultrasonic pulse echo system as set forth in claim 6, and means acting upon said control means for causing said timing means after the receipt of a predetermined quantity of second output signals to provide said first output signal for periodically updating said correction factor.

8. In an ultrasonic pulse echo system as set forth in claim 6, said timing means including a counter operating at a counting frequency of at least 100 MHz.

* * * * *